(12) United States Patent
Raffle et al.

(10) Patent No.: US 8,955,973 B2
(45) Date of Patent: Feb. 17, 2015

(54) METHOD AND SYSTEM FOR INPUT DETECTION USING STRUCTURED LIGHT PROJECTION

(71) Applicant: Google Inc., Mountain View, CA (US)

(72) Inventors: Hayes Solos Raffle, Palo Alto, CA (US); Thad Eugene Starner, Mountain View, CA (US); Josh Weaver, San Jose, CA (US); Edward Allen Keyes, Mountain View, CA (US)

(73) Assignee: Google Inc., Mountain View, CA (US)

( * ) Notice: Subject to any disclaimer, the term of this patent is extended or adjusted under 35 U.S.C. 154(b) by 92 days.

(21) Appl. No.: 13/631,594

(22) Filed: Sep. 28, 2012

(65) Prior Publication Data

US 2013/0176533 A1    Jul. 11, 2013

Related U.S. Application Data

(60) Provisional application No. 61/583,685, filed on Jan. 6, 2012.

(51) Int. Cl.
*A61B 3/14* (2006.01)
*A61B 3/113* (2006.01)
*G01B 11/25* (2006.01)
*G01B 11/16* (2006.01)
(Continued)

(52) U.S. Cl.
CPC .............. *A61B 3/113* (2013.01); *G01B 11/167* (2013.01); *G01B 11/2513* (2013.01); *A61F 2009/00846* (2013.01); *G01B 11/25* (2013.01); *G06F 3/013* (2013.01)
USPC ............................ 351/209; 351/210; 351/246

(58) Field of Classification Search
CPC .......... A61B 3/11; A61B 3/111; A61B 3/112; A61B 3/113; A61B 3/10; A61B 3/14; A61B 3/145; A61B 3/15; A61B 3/152; A61F 2009/00846; G01B 11/167; G01B 11/25; G01B 11/2513
USPC .................................................. 351/209, 210
See application file for complete search history.

(56) References Cited

U.S. PATENT DOCUMENTS 4,836,670 A  *  6/1989  Hutchinson .................... 351/210
5,159,361 A  *  10/1992  Cambier et al. ............... 351/212
5,345,281 A  *  9/1994  Taboada et al. ............... 351/210
(Continued)

FOREIGN PATENT DOCUMENTS

KR      10-0703930 B1    4/2007
WO         0133282 A1    10/2001
WO      2006012679 A1    2/2006

OTHER PUBLICATIONS

International Search Report for PCT/US2012/065038 mailed Mar. 20, 2013.

*Primary Examiner* — Thomas K Pham
*Assistant Examiner* — Nicholas Pasko
(74) *Attorney, Agent, or Firm* — McDonnell Boehnen Hulbert & Berghoff LLP

(57) ABSTRACT

Exemplary methods and systems help provide for tracking an eye. An exemplary method may involve: causing the projection of a pattern onto an eye, wherein the pattern comprises at least one line, and receiving data regarding deformation of the at least one line of the pattern. The method further includes correlating the data to iris, sclera, and pupil orientation to determine a position of the eye, and causing an item on a display to move in correlation with the eye position.

16 Claims, 6 Drawing Sheets

(51) Int. Cl.
*A61F 9/008* (2006.01)
*G06F 3/01* (2006.01)

(56) References Cited

U.S. PATENT DOCUMENTS

| | | | |
|---|---|---|---|
| 6,003,991 A | 12/1999 | Viirre | |
| 6,283,954 B1 * | 9/2001 | Yee | 606/5 |
| 6,315,773 B1 * | 11/2001 | Frey et al. | 606/12 |
| 6,367,931 B2 * | 4/2002 | Lai | 351/209 |
| 6,542,081 B2 * | 4/2003 | Torch | 340/575 |
| 6,659,611 B2 | 12/2003 | Amir et al. | |
| 6,905,209 B2 * | 6/2005 | Mihashi et al. | 351/221 |
| 7,306,337 B2 | 12/2007 | Ji et al. | |
| 7,309,126 B2 * | 12/2007 | Mihashi et al. | 351/205 |
| 7,377,645 B2 | 5/2008 | Wrobel et al. | |
| 7,809,160 B2 | 10/2010 | Vertegaal et al. | |
| 7,878,654 B2 * | 2/2011 | Mattioli et al. | 351/211 |
| 2010/0220291 A1 * | 9/2010 | Horning et al. | 351/210 |
| 2011/0069277 A1 * | 3/2011 | Blixt et al. | 351/210 |
| 2011/0157553 A1 | 6/2011 | Moeller et al. | |

* cited by examiner

US 8,955,973 B2

METHOD AND SYSTEM FOR INPUT DETECTION USING STRUCTURED LIGHT PROJECTION

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mounted displays" (HMDs). A head-mounted display places a graphic display or displays close to one or both eyes of a wearer. To generate the images on a display, a computer processing system may be used. Such displays may occupy a wearer's entire field of view, or only occupy part of wearer's field of view. Further, head-mounted displays may be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming.

SUMMARY

In one aspect, an exemplary computer-implemented method may involve: causing the projection of a pattern onto an eye, wherein the pattern comprises at least one line, and receiving data regarding deformation of the at least one line of the pattern. The method further includes correlating the data to iris, sclera, and pupil orientation to determine a position of the eye, and causing an item on the wearable computing system to move in correlation with the eye position.

In another aspect, an exemplary system may include a non-transitory computer-readable medium and program instructions stored on the non-transitory computer-readable medium. The program instructions may be executable by at least one processor to cause a projection of a pattern onto an eye, wherein the pattern comprises at least one line, receive data regarding deformation of the at least one line of the pattern, correlate the data to iris, sclera, and pupil orientation to determine the position of the eye, and cause an item on a display to move in correlation with the eye position.

In yet another embodiment, a computer-implemented method is provided. The method comprises projecting a pattern onto an eye, wherein the pattern comprises at least one line, receiving data regarding deformation of the at least one line of the pattern, correlating the data to iris, sclera, and pupil orientation, combined with eye dynamics, to determine a position of the eye, and causing an item on a display to move in correlation with the position.

These as well as other aspects, advantages, and alternatives, will become apparent to those of ordinary skill in the art by reading the following detailed description, with reference where appropriate to the accompanying drawings.

DETAILED DESCRIPTION

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Overview

An exemplary embodiment may be implemented by or take the form of a head-mountable display (HMD), or a computing system that receives data from an HMD, such as a cloud-based server system. The HMD may include an inward-facing camera or cameras that are configured to capture images of the wearer's eye or eyes. The images of the wearer's eye may be video and/or still images, depending upon the particular implementation.

To track the movement, position, and/or orientation of the wearer's eye, structured light may be projected from the HMD onto the eye. The concavity and convexity of the iris and sclera deform the structured light, providing an indication as to the position and orientation of the eye for a given time.

I. A Head-Mounted Display with Dynamic Eyebox

Figure 1:
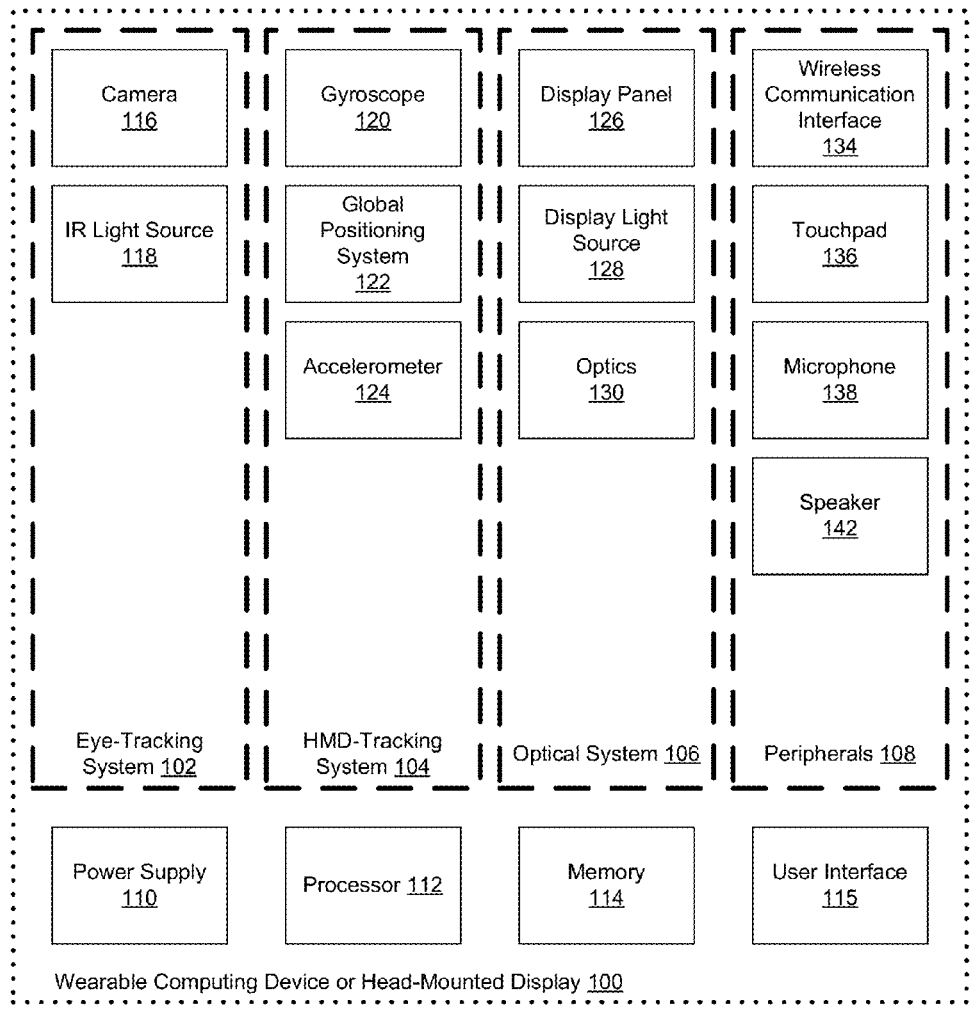
FIG. 1 is a schematic diagram of a wearable computing device, in accordance with an example embodiment.

FIG. 1 is a schematic diagram of a wearable computing device or a head-mounted display (HMD) 100, in accordance with an example embodiment. As shown, the HMD 100 includes an eye-tracking system 102, an HMD-tracking system 104, an optical system 106, peripherals 108, a power supply 110, a processor 112, a memory 114, and a user interface 115. The eye-tracking system 102 may include hardware such as a camera 116 and at least one infrared light source 118. The HMD-tracking system 104 may include a gyroscope 120, a global positioning system (GPS) 122, and an accelerometer 124. The optical system 106 may include, in one embodiment, a display panel 126, a display light source 128, and optics 130. The peripherals 108 may include a wireless communication interface 134, a touchpad 136, a microphone 138, a camera 140, and a speaker 142.

In an example embodiment, HMD 100 includes a see-through display. Thus, the wearer of HMD 100 may observe a portion of the real-world environment, i.e., in a particular field of view provided by the optical system 106. In the example embodiment, HMD 100 is operable to display virtual images that are superimposed on the field of view, for example, to provide an "augmented reality" experience. Some of the virtual images displayed by HMD 100 may be superimposed over particular objects in the field of view. HMD 100 may also display images that appear to hover within the field of view instead of being associated with particular objects in the field of view.

Components of the HMD 100 may be configured to work in an interconnected fashion with other components within or outside their respective systems. For instance, in an example embodiment, the camera 116 in the eye-tracking system 102 may image one or both of the HMD wearer's eyes. The camera 116 may deliver image information to the processor 112, which may access the memory 114 and make a determination regarding the position of the HMD wearer's eye or eyes. The processor 112 may also receive input from the GPS unit 122, the gyroscope 120, and/or the accelerometer 124 to determine HMD-to-eye relative position data. Subsequently, the processor 112 may control the user interface 115 and the display panel 126 to display virtual images to the HMD wearer that may be adjusted to compensate for displacements away from a normal viewing position.

HMD 100 could be configured as, for example, eyeglasses, goggles, a helmet, a hat, a visor, a headband, or in some other form that can be supported on or from the wearer's head. Further, HMD 100 may be configured to display images to both of the wearer's eyes, for example, using two see-through displays. Alternatively, HMD 100 may include only a single see-through display and may display images to only one of the wearer's eyes, either the left eye or the right eye.

The HMD 100 may also represent an opaque display configured to display images to one or both of the wearer's eyes without a view of the real-world environment. For instance, an opaque display or displays could provide images to both of the wearer's eyes such that the wearer could experience a virtual reality version of the real world. Alternatively, the HMD wearer may experience an abstract virtual reality environment that could be substantially or completely detached from the real world. Further, the HMD 100 could provide an opaque display for a first eye of the wearer as well as provide a view of the real-world environment for a second eye of the wearer.

A power supply 110 may provide power to various HMD components and could represent, for example, a rechargeable lithium-ion battery. Various other power supply materials and types known in the art are possible.

The functioning of the HMD 100 may be controlled by a processor 112 that executes instructions stored in a non-transitory computer readable medium, such as the memory 114. Thus, the processor 112 in combination with instructions stored in the memory 114 may function as a controller of HMD 100. As such, the processor 112 may control the user interface 115 to adjust the images displayed by HMD 100. The processor 112 may also control the wireless communication interface 134 and various other components of the HMD 100. The processor 112 may additionally represent a plurality of computing devices that may serve to control individual components or subsystems of the HMD 100 in a distributed fashion.

In addition to instructions that may be executed by the processor 112, the memory 114 may store data that may include a set of calibrated wearer eye pupil positions and a collection of past eye pupil positions. Thus, the memory 114 may function as a database of information related to gaze direction and/or HMD wearer eye location. Such information may be used by HMD 100 to anticipate where the wearer will look and determine what images are to be displayed to the wearer. Within the context of the invention, eye pupil positions could also be recorded relating to a 'normal' or a 'calibrated' viewing position. Eye box or other image area adjustment could occur if the eye pupil is detected to be at a location other than these viewing positions.

In addition, information may be stored in the memory 114 regarding possible control instructions that may be enacted using eye movements. For instance, two consecutive wearer eye blinks may represent a control instruction directing the HMD 100 to capture an image using camera 140. Another possible embodiment may include a configuration such that specific eye movements may represent a control instruction. For example, an HMD wearer may lock or unlock the user interface 115 with a series of predetermined eye movements.

Control instructions could be based on dwell-based selection of a target object. For instance, if a wearer fixates visually upon a particular virtual image or real-world object for longer than a predetermined time period, a control instruction may be generated to select the virtual image or real-world object as a target object. Many other control instructions are possible.

The HMD 100 may include a user interface 115 for providing information to the wearer or receiving input from the wearer. The user interface 115 could be associated with, for example, the displayed virtual images and/or one or more input devices in peripherals 108, such as touchpad 136 or microphone 138. The processor 112 may control the functioning of the HMD 100 based on inputs received through the user interface 115. For example, the processor 112 may utilize user input from the user interface 115 to control how the HMD 100 displays images within a field of view or to determine what images the HMD 100 displays.

An eye-tracking system 102 may be included in the HMD 100. In an example embodiment, an eye-tracking system 102 may deliver information to the processor 112 regarding the eye position of a wearer of the HMD 100. The eye-tracking data could be used, for instance, to determine a direction in which the HMD wearer may be gazing. The processor 112 could determine target objects among the displayed images based on information from the eye-tracking system 102. The processor 112 may control the user interface 115 and the display panel 126 to adjust the target object and/or other displayed images in various ways. For instance, an HMD wearer could interact with a mobile-type menu-driven user interface using eye gaze movements.

The camera 116 may be utilized by the eye-tracking system 102 to capture images of a viewing location associated with the HMD 100. Thus, the camera 116 may image the eye of an HMD wearer that may be located at the viewing location. The images could be either video images or still images. The images obtained by the camera 116 regarding the HMD wearer's eye may help determine where the wearer is looking within the HMD field of view, for instance by allowing the processor 112 to ascertain the location of the HMD wearer's eye pupil. Analysis of the images obtained by the camera 116 could be performed by the processor 112 in conjunction with the memory 114 to determine, for example, a gaze direction.

The imaging of the viewing location could occur continuously or at discrete times depending upon, for instance, HMD wearer interactions with the user interface 115 and/or the state of the infrared light source 118 which may serve to illuminate the viewing location. The camera 116 could be integrated into the optical system 106 or mounted on the HMD 100. Alternatively, the camera 116 could be positioned apart from the HMD 100 altogether. The camera 116 could be configured to image primarily in the infrared. The camera 116 could additionally represent a conventional visible light camera with sensing capabilities in the infrared wavelengths. Imaging in other wavelength ranges is possible.

The infrared light source 118 could represent one or more infrared light-emitting diodes (LEDs) or infrared laser diodes that may illuminate a viewing location. One or both eyes of a wearer of the HMD 100 may be illuminated by the infrared light source 118.

The eye-tracking system 102 could be configured to project structured light onto the eye surface, and to acquire images of the structured light as applied to the eye surface. The eye-tracking system could be configured to obtain and retain data regarding physical properties of the eye, such as eye anatomy and dynamics, by using a Kalman filter for example. Examples of physical properties of the eye that aid in determining when eye-tracking is providing poor results include multiple saccades without the minimum 100-200 millisecond (ms) refractory period, saccades greater than 40 degrees, saccades lasting more than 300 ms, and fixations lasting more than 600 ms. In addition, an eye-tracking result that includes an improbable eye dynamic, such as a translation of the eyeball out of the head or too far into the head, for example, may be determined using eye anatomy and/or dynamics. In practice, a combination of these techniques may be used for eye tracking at a desired level of robustness. Other imaging and tracking methods are possible.

The eye-tracking system 102 could be used to determine the relative position of the display with respect to the HMD wearer's eye. For example, by imaging the shape of the lines or shapes of a pattern of structured light on the HMD wearer's eye(s), combined with the eye anatomy and eye dynamics, the position of the eye could be sensed.

The HMD-tracking system 104 could be configured to provide an HMD position and an HMD orientation to the processor 112.

The gyroscope 120 could be a microelectromechanical system (MEMS) gyroscope, a fiber optic gyroscope, or another type of gyroscope known in the art. The gyroscope 120 may be configured to provide orientation information to the processor 112. The GPS unit 122 could be a receiver that obtains clock and other signals from GPS satellites and may be configured to provide real-time location information to the processor 112. The HMD-tracking system 104 could further include an accelerometer 124 configured to provide motion input data to the processor 112. The HMD-tracking system 104 could include other sensors, such as a proximity sensor.

The optical system 106 could include components configured to provide virtual images at a viewing location. The viewing location may correspond to the location of one or both eyes of a wearer of an HMD 100. The components of the optical system 106 could include a display panel 126, a display light source 128, and optics 130. These components may be optically and/or electrically-coupled to one another and may be configured to provide viewable images at a viewing location. As mentioned above, one or two optical systems 106 could be provided in an HMD apparatus. In other words, the HMD wearer could view virtual images in one or both eyes, as provided by one or more optical systems 106. Also, as described above, the optical system(s) 106 could include an opaque display and/or a see-through display, which may allow a view of the real-world environment while providing superimposed virtual images.

Various peripheral devices 108 may be included in the HMD 100 and may serve to provide information to and from a wearer of the HMD 100. In one example, the HMD 100 may include a wireless communication interface 134 for wirelessly communicating with one or more devices directly or via a communication network. For example, wireless communication interface 134 could use 3G cellular communication, such as CDMA, EVDO, GSM/GPRS, or 4G cellular communication, such as WiMAX or LTE. Alternatively, wireless communication interface 134 could communicate with a wireless local area network (WLAN), for example, using WiFi. In some embodiments, wireless communication interface 134 could communicate directly with a device, for example, using an infrared link, Bluetooth, or ZigBee. The wireless communication interface 134 could interact with devices that may include, for example, components of the HMD 100 and/or externally-located devices.

Although FIG. 1 shows various components of the HMD 100 (i.e., wireless communication interface 134, processor 112, memory 114, camera 116, display panel 126, GPS 122, and user interface 115) as being integrated into HMD 100, one or more of these components could be physically separate from HMD 100. For example, the camera 116 could be mounted on the wearer separate from HMD 100. Thus, the HMD 100 could be part of a wearable computing device in the form of separate devices that can be worn on or carried by the wearer. The separate components that make up the wearable computing device could be communicatively coupled together in either a wired or wireless fashion.

Figure 2A:
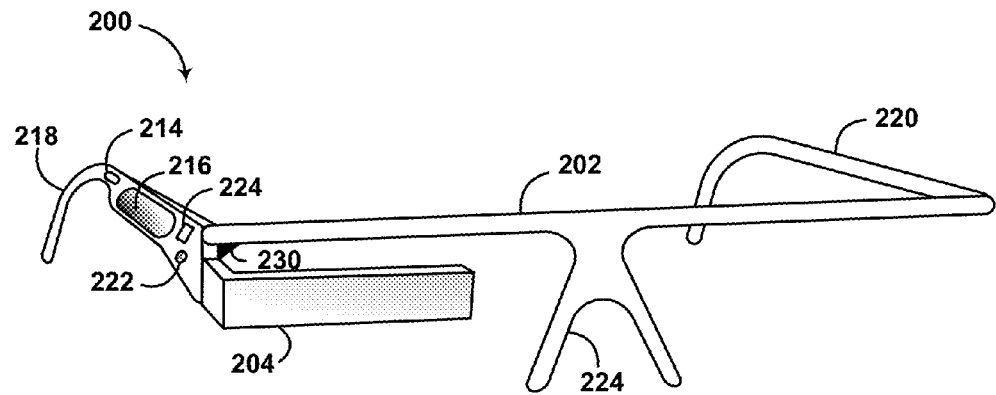
FIG. 2A is a perspective view of a head-mounted display, in accordance with an example embodiment.

FIGS. 2A, 2B, 2C, and 2D illustrate example head-mounted displays that have an eyeglasses frame format. FIG. 2A is a perspective view of a head-mounted display (HMD) 200, in accordance with an example embodiment. The HMD 200 has a frame 202 that could include nosepiece 224 and earpieces 218 and 220. The frame 202, nosepiece 224, and earpieces 218 and 220 could be configured to secure the HMD 200 to a wearer's face via a wearer's nose and ears. Each of the frame elements, 202, 224, 218, and 220 may be formed of a solid structure of plastic and/or metal, or may be formed of a hollow structure of similar material so as to allow wiring and component interconnects to be internally routed through the HMD 200. Other materials may be possible as well.

The earpieces 218 and 220 could be attached to projections that extend away from the frame 202 and could be positioned behind a wearer's ears to secure the HMD 200 to the wearer. The projections could further secure the HMD 200 to the wearer by extending around a rear portion of the wearer's head. Additionally or alternatively, for example, the HMD 200 could connect to or be affixed within a head-mounted helmet structure. Other possibilities exist as well.

An optical system 204 could be attached the frame 202. The optical system 204 could be formed of any material that can suitably display a projected image or graphic. At least a portion of the optical system 204 could be sufficiently transparent to allow a wearer to see through a lens element. The optical system 204 may thus facilitate an augmented reality or a heads-up display where the projected image or graphic is superimposed over a real-world view as perceived by the wearer through optical system 204.

The HMD 200 may include a computer 214, a touch pad 216, a microphone 222, a button 224, a camera 230, and the optical system 204. The computer 214 is shown to be positioned on the extending side arm of the HMD 200; however, the computer 214 may be provided on other parts of the HMD 200 or may be positioned remote from the HMD 200 (e.g., the computer 214 could be wire- or wirelessly-connected to the HMD 200). The computer 214 could include a processor and memory, for example. The computer 214 may be configured to receive and analyze data from sensory devices, user-interfaces, or both, and generate images for output by the optical system 204.

Although not shown in FIG. 2A, 2B, 2C, or 2D, additional sensors could be incorporated into HMD 200. Such sensors may include one or more of a gyroscope, an accelerometer, and/or a proximity sensor, for example. Other sensing devices may be included in HMD 200.

The touch pad 216 is shown on an extending side arm of the HMD 200. However, the touch pad 216 may be positioned on other parts of the HMD 200. Also, more than one touch pad may be present on the HMD 200. The touch pad 216 may be used by a HMD wearer to input commands. The touch pad 216 may sense at least one of a position and a movement of a finger via capacitive sensing, resistance sensing, or a surface acoustic wave process, among other possibilities. The touch pad 216 may be capable of sensing finger movement in a direction parallel or planar to the pad surface, in a direction normal to the pad surface, or both, and may also be capable of sensing a level of pressure applied to the pad surface. The touch pad 216 may be formed of one or more translucent or transparent insulating layers and one or more translucent or transparent conducting layers. Edges of the touch pad 216 may be formed to have a raised, indented, or roughened surface, so as to provide tactile feedback to an HMD wearer when the wearer's finger reaches the edge, or other area, of the touch pad 216. If more than one touch pad is present, each touch pad may be operated independently, and may provide a different function.

The optical system 204 could represent, for instance, an at least partially reflective surface upon which images could be projected using a projector (not shown). For instance, optical system 204 could act as a combiner in a light projection system and may include a coating that reflects the light projected onto them from projectors. In some embodiments, a reflective coating may be omitted (e.g., when the projectors are scanning laser devices). The projected images could be thus viewable to an HMD wearer.

Although the optical system 204 is depicted as presented to the right eye of the HMD wearer, it will be understood that other example embodiments could include an optical system for the HMD wearer's left eye, dual optical system for both eyes, or a single optical system viewable by both eyes. Additionally, optical system 204 could be integrated into lenses (e.g., glasses lenses) located in front of one or both eyes of the HMD wearer.

In alternative embodiments, other types of display elements may be used in optical system 204. For example, optical system 204 may include: a transparent or semi-transparent matrix display, such as an electroluminescent display or a liquid crystal display, one or more waveguides for delivering an image to the HMD wearer's eyes, or other optical elements capable of delivering an in-focus near-to-eye image to the wearer. A corresponding display driver may be disposed within the frame 202 for driving such a matrix display. Alternatively or additionally, a laser or light-emitting diode (LED) source and scanning system could be used to draw a raster display directly onto the retina of one or more of the wearer's eyes. Other possibilities exist as well.

Figure 2B:
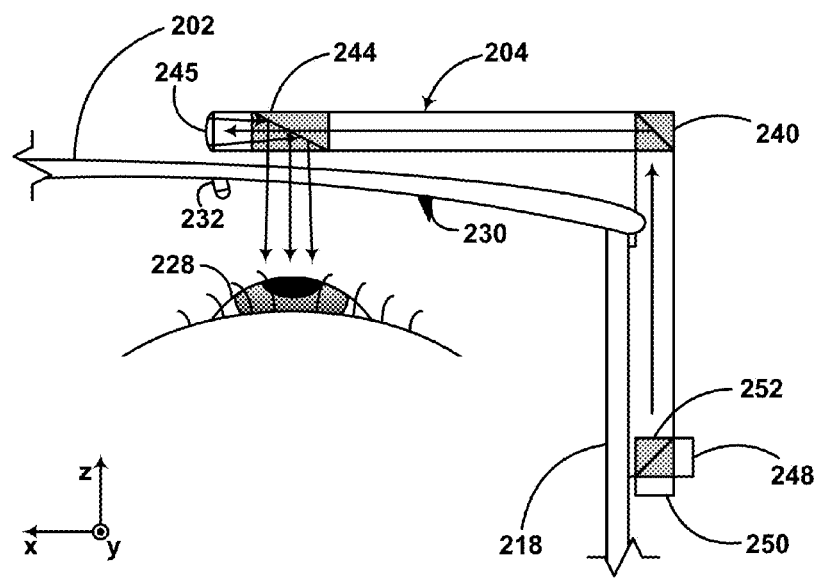
FIG. 2B is a top view of the head-mounted display in FIG. 2A, in accordance with an example embodiment.

FIG. 2B is a top view of the HMD 200 illustrated in FIG. 2A and described above. In an example embodiment, optical system 204 could be attached onto or integrated into HMD 200. Additionally, the HMD 200 may include one or more eye-tracking systems, which may be configured to track the eye position of one or both eyes of the HMD wearer. The eye-tracking systems may each include one or more infrared light sources 232 and one or more cameras 230. Each eye tracking system could be configured to image one or both of the HMD wearer's eyes. Alternatively, one eye-tracking system could be used to track both eyes of a HMD wearer.

The optical system 204 could include a display light source 248, a display panel 250, a display beam splitter 252, a proximal beam splitter 244, and an image former 245. In one embodiment, the optical element could include a distal beam splitter 240. Further, although one optical system 242 is shown in FIGS. 2A, 2B, 2C, and 2D, in some embodiments, optical systems 204 could be provided to both eyes of an HMD wearer. Those with skill in the art will understand there are many other configurations possible in such an optical system and those configurations are implicitly contemplated herein.

The display panel 250 could be configured to generate a light pattern from which virtual and/or real images could be formed. The display panel 250 could be an emissive display, such as an organic light-emitting diode (OLED) display. Alternatively, the display panel 250 may be a liquid-crystal on silicon (LCOS) or a micro-mirror display such as a digital light projector (DLP) that generates the light pattern by spatially modulating light from the display light source 248. The display light source 248 may include, for example, one or more light-emitting diodes (LEDs) and/or laser diodes. The light pattern generated by the display panel 250 could be monochromatic, or it could include multiple colors (such as red, green, and blue) to provide a color gamut for the virtual and/or real images.

In an example embodiment, the distal beam splitter 240 could substantially reflect light from display panel 250 towards the proximal beam splitter 244 and image former 245. Image former 245 may include a concave mirror or other optical component that forms a virtual image that is viewable through the proximal beam splitter 244. In this manner, a viewable image could be delivered to the HMD wearer's eye 228.

Figure 2C:
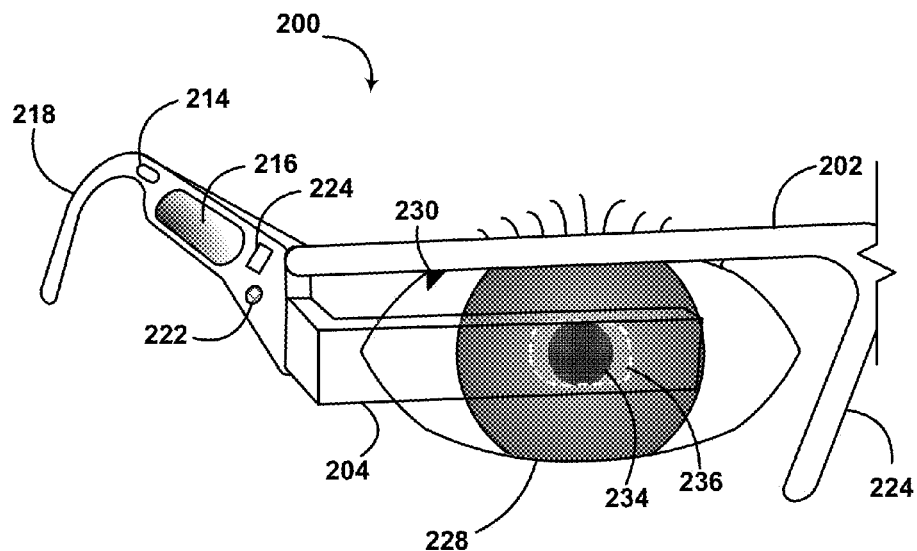
FIG. 2C is a perspective view of a head-mounted display, in accordance with an example embodiment.

FIG. 2C is a perspective view of the HMD 200 that provides a close-up view of optical system 204 and the right eye 228 of the HMD wearer. As shown, a pattern 236 may be projected on an eye 228 of a HMD wearer. The position of the pattern 236 may be based on the relative position of the HMD 200 with respect to the HMD wearer's eye 228.

In an example embodiment, a camera 230 could image the HMD wearer's eye 228 with the pattern 236 overlayed on the eye 228. The camera 230 could be an infrared camera. The acquired images could be processed with image recognition algorithms (e.g., Canny edge detection) so as to determine a position of the display area with respect to the HMD wearer's eye 228. A controller could use the determined position as an input to control software and/or hardware so as to keep the displayed images centered on the HMD wearer's eye 228.

Figure 2D:
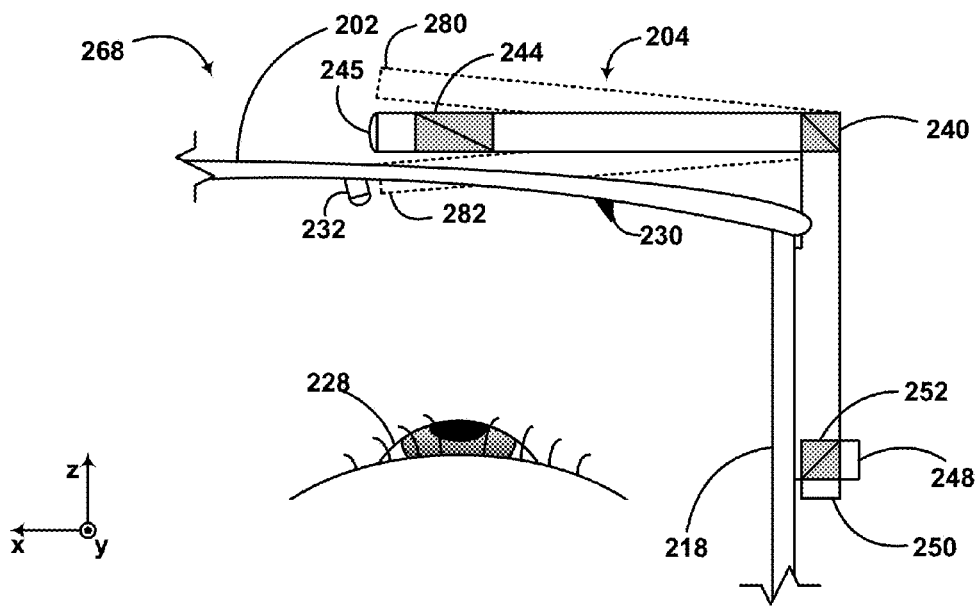
FIG. 2D is a top view of the head-mounted display in FIG. 2C, in accordance with an example embodiment.

FIG. 2D is a top view of the HMD 200. A depicted scenario 268 illustrates how HMD movement relative to a viewing position could cause a keystoning effect. In one embodiment, an optical system 204 could be integrated or attached to a frame 202. Due to HMD wearer movement, adjustment of the optical system 204, and other displacements, the HMD optical system could be presented to the HMD wearer throughout a range of depths and angles (e.g., optical system locations 280 and 282).

The display area could include a display area pixel set that could be a superset of the image area and corresponding image area pixel set. By subsetting the image area pixel set within the display area pixel set, vector graphics could be foreshortened or otherwise adjusted due to keystone effects. In some instances, the image area pixel set could be the same as the display area pixel set, for instance, if the HMD is not moving with respect to the HMD wearer. Depending upon the amount of relative movement detected between the HMD and the HMD wearer, the image area pixel set could be subset within the display area pixel set to a greater or lesser degree.

Figure 3:
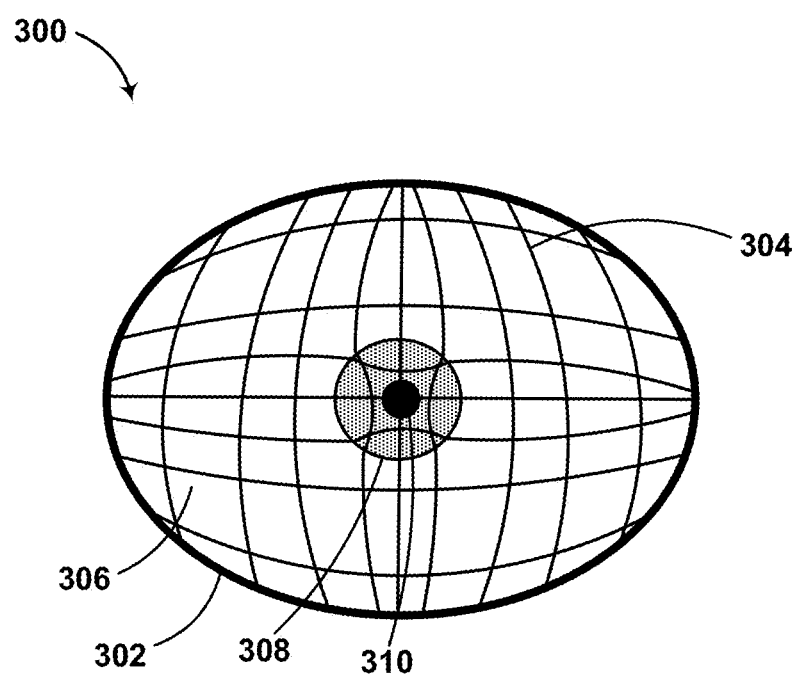
FIG. 3 is a front view of an eye of a wearer of a head-mounted display, in accordance with an example embodiment.

FIG. 3 is an example 300 of a front view of an eye of a wearer of a head-mounted display, in which the structured light could be projected onto the eye. Example 300 shows an HMD wearer's eye 302 and a grid or pattern 304 that is projected over the eye 302. The eye comprises a sclera 306, an iris 308, and a pupil 310. The pattern 304 may comprise a plurality of horizontal and vertical lines. In alternative embodiments, the pattern 304 may comprise a pattern of a plurality of curved or circular lines, for example. Other patterns may be contemplated as well.

As shown in example 300, the pattern 304 is reflected as deformed once projected onto the eye. The deformed lines of the pattern 304 over the sclera 306 comprise lines that bow outward. This bowed outward line shape is due to the convexity of the sclera 306. The deformed lines of the pattern 304 over the iris 308 comprise lines that bow inward, due to the concave surface of the iris 308. The pupil 310 does not reflect any lines.

The redundancy of the pattern comprising the pattern 304 ensures that some region over the eye will be trackable. Further, ambient glints can be ignored because the glints will not match the pattern 304. The deformation of the lines over the sclera 306 and the iris 308 can be combined with dark pupil tracking to more accurately track the eye's position.

In some examples, knowledge of the eye anatomy and dynamics may be combined with the pattern 304 to determine the direction of the eye's gaze. More specifically, the eye movement in the upward and downward directions, as well as the eye's side to side rotation is controlled by four major muscles, in addition to other minor muscles for rotating around the visual axis. The muscles apply force, making eye motion predictable using a Kalman filter. Additionally, knowledge regarding eye saccades allows for the prediction of where the eye is relative to a previous frame at a point in time. Furthermore, noisy observations (e.g., situations there the projected pattern 304 is partially washed out by glints in the environment) may be combined with knowledge of eye dynamics to come up with a more a more optimal estimate of where the eye is pointing.

Using eye-tracking, the relative position of the HMD wearer's eye to the HMD may be monitored. Thus, when relative movement occurs, the HMD may control the optical system to move the images in an effort to maintain them within the HMD user's view. The image movement could include scaling of some or all of the displayed images. Such scaling may include shrinking (or subsetting) the area of the displayed images. Further, the entire scaled set of displayed images could be moved based on the relative movement of the HMD wearer's eye.

Feedback from the eye-tracking system may control the HMD to continue moving the images in a same direction, to move images in a different direction, or to select an item displayed.

II. Eye-Tracking Methods Based on Structured Light

Figure 4:
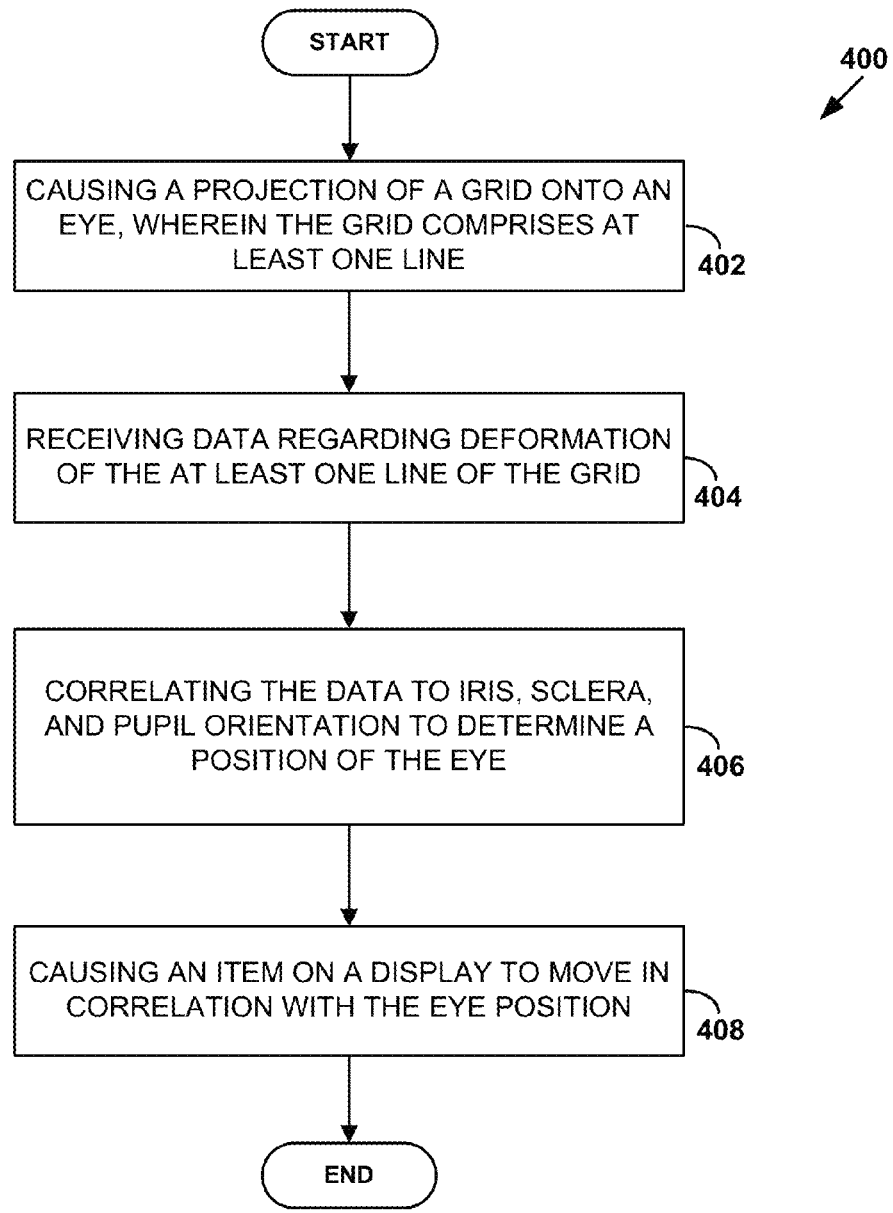
FIG. 4 is a flow chart illustrating a method for eye-tracking, in accordance with an example embodiment.

FIG. 4 is a flow chart illustrating a method for eye-tracking, in accordance with an example embodiment. Method 400 may be carried out in whole or in part by a wearable computer having a head-mountable display, but may be carried out by other devices or systems as well. Method 400 may be implemented to track a user's eye movements on a wearable computer such as an HMD.

Accordingly, exemplary methods may be described by way of example herein as being implemented by an HMD. However, it should be understood that an exemplary method may be implemented in whole or in part by other types of computing devices. For example, an exemplary method may be implemented in whole or in part by a server system, which receives data from a device such as an HMD. As further examples, an exemplary method may be implemented in whole or in part by a mobile phone, tablet computer, or laptop computer equipped with a camera, by a network-enabled camera, and/or by other computing devices configured to capture and/or receive eye-image data. Other examples of computing devices or combinations of computing devices that can implement an exemplary method are possible.

As shown by block 402, the exemplary method 400 involves causing the projection of a pattern onto an eye, wherein the pattern comprises at least one line. The line of the projected pattern may extend over at least the sclera and the pupil of the eye. The pattern may extend across the entire surface of the eye. The pattern may comprise a grid of squares. The squares may comprise alternating light squares and dark squares, such that each dark square is surrounded on all sides by light squares, and vice-versa. The grid may initially comprise large, coarsely defined squares, which can be made to be incrementally finer as desired for a particular application.

The wearable computing system then receives data regarding deformation of the at least one line of the pattern, as shown by block 404. The deformation of the line projected over the sclera is reflected as a line that is bowed outward from its original position. The deformation of the line projected over the iris is reflected as a line that is bowed inward from its original position. The pupil does not reflect the line; thus the line will not show over the portion of the eye comprising the pupil.

At block 406, the method includes correlating the data to iris, sclera, and pupil orientation to determine a position of the eye.

In response to determining the position of the eye, the method 400 includes providing an input method to a user interface in correlation with the eye position, as shown by block 408. A processor on the wearable computing system may execute instructions to cause the display to move in correlation with the eye position, or to cause for the selection of an item on the display.

Figure 5:
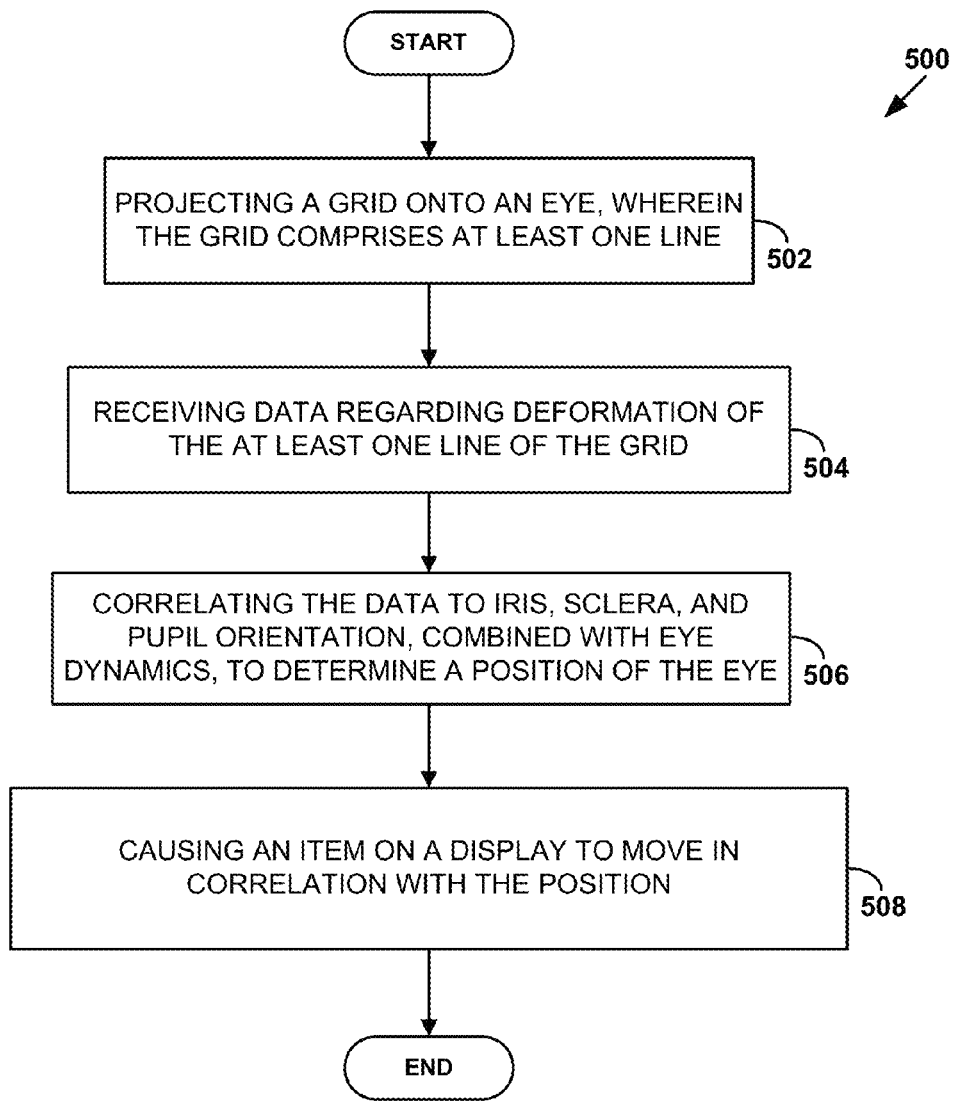
FIG. 5 is a flow chart illustrating a method for eye-tracking, in accordance with an example embodiment.

FIG. 5 is another flow chart illustrating a method for eye-tracking, in accordance with an example embodiment. Method 500 is described by way of example as being carried out by a wearable computer, but may be carried out by other devices or systems as well. While FIG. 4 illustrates an exemplary method 400 in which an eye is tracked based on a projected grid pattern, FIG. 5 illustrates an exemplary method 500 in which an eye is tracked based on a hybrid of both eye dynamics and a projected pattern.

As shown by block 502, the exemplary method 500 involves causing a projection of a pattern onto an eye, wherein the pattern comprises at least one line. The at least one line may extend across at least the sclera and the pupil of the eye. The pattern may comprise a grid of squares. The squares may comprise alternating light squares and dark squares, such that each dark square is surrounded on all sides by light squares, and vice-versa. The grid may initially comprise large, coarsely defined squares, which can be made to be incrementally finer as desired for a particular application. A diffraction grating pattern generator may project the pattern onto the eye. In another example, a mini-projector may project the pattern onto the eye. Several grids of varying fineness may be projected onto the eye to precisely determine the edges of the pupil, limbus, and other parts of the eye. In another example, the pattern may comprise circles, or any other pattern with features that can be used to track the eye anatomy.

At block 504, the method 500 involves receiving data regarding deformation of the at least one line of the pattern. The deformation of the line projected over the sclera shows as a line that is bowed outward from its original position. The deformation of the line projected over the iris shows as a line that is bowed inward from its original position. The pupil does not reflect the line; thus the line will not show over the portion of the eye comprising the pupil.

At block 506, the method includes correlating the data to iris, sclera, and pupil orientation, combined with information regarding eye dynamics, to determine a position of the eye. The information regarding eye dynamics may include information regarding forces exerted by eye muscles and saccades and may be used to predict where the eye is relative to a previous frame at a point in time.

In response to determining the eye position, the method includes providing an input method to a user interface in correlation with the position, as shown by block 508.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method comprising:
   a light projector projecting a pattern of light onto an eye, wherein the pattern comprises at least one line;
   receiving data regarding a first deformation of the at least one line of the pattern at a first time, wherein the first deformation of the at least one line comprises the line bowing outward when projected over the sclera or the line bowing inward when projected over the iris;
   receiving data regarding a second deformation of the at least one line of the pattern at a second time that is subsequent to the first time, wherein the second deformation of the at least one line of the pattern comprises the line bowing outward relative to the first deformation of the at least one line or the line bowing inward relative to the first deformation of the at least one line; and
   correlating the data to at least one of iris, sclera, and pupil orientation to determine a position of the eye.

2. A system comprising:
   a non-transitory computer-readable medium; and
   program instructions stored on the non-transitory computer-readable medium which, when executed by at least one processor, cause the system to:
   cause a light projector to project a pattern of light onto an eye, wherein the pattern comprises at least one line;
   receive data regarding a first deformation of the at least one line of the pattern at a first time, wherein the first deformation of the at least one line comprises the line bowing outward when projected over the sclera or the line bowing inward when projected over the iris;
   receive data regarding a second deformation of the at least one line of the pattern at a second time that is subsequent to the first time, wherein the second deformation of the at least one line of the pattern comprises the line bowing outward relative to the first deformation of the at least one line or the line bowing inward relative to the first deformation of the at least one line;
   correlate the data to iris, sclera, and pupil orientation to determine the position of the eye; and
   cause an item on a display to move in correlation with the eye position.

3. A method comprising:
   a light projector projecting a pattern of light onto an eye, wherein the pattern comprises at least one line;
   receiving data regarding a first deformation of the at least one line of the pattern at a first time, wherein the first deformation of the at least one line comprises the line bowing outward when projected over the sclera or the line bowing inward when projected over the iris;
   receiving data regarding a second deformation of the at least one line of the pattern at a second time that is subsequent to the first time, wherein the second deformation of the at least one line of the pattern comprises the line bowing outward relative to the first deformation of the at least one line or the line bowing inward relative to the first deformation of the at least one line;
   correlating the data to iris, sclera, and pupil orientation, combined with eye dynamics, to determine a position of the eye; and
   causing an item on a display to move in correlation with the position.

4. The method of claim 1, wherein the pattern comprises a plurality of vertical and horizontal lines.

5. The method of claim 1, wherein at least one line is not visible over the pupil.

6. The method of claim 1, wherein correlating further comprises matching a deformed portion of the line that is bowed outward as being the portion of the line that is over the sclera.

7. The method of claim 1, wherein correlating further comprises matching a deformed portion of the line that is bowed inward as being the portion of the line that is over the iris.

8. The method of claim 1, further comprising monitoring eye movement with one or more cameras.

9. The method of claim 1, further comprising causing an item on a display to move in correlation with the eye position.

10. The method of claim 1, further comprising:
    modeling glints caused by an ambient environment;
    determining where the glints are relative to the eye;
    predicting how the glints will change as the eye moves using data concerning the dynamics of the eye; and
    combining the prediction with the correlation of the pattern and sclera, iris, and pupil data to track the eye.

11. The system of claim 2, wherein the pattern comprises a plurality of vertical and horizontal lines.

12. The system of claim 2, wherein the at least one line is not visible over the pupil.

13. The system of claim 2, wherein correlating further comprises matching a deformed portion of the line that is bowed outward as being the portion of the line that is over the sclera.

14. The system of claim 2, wherein correlating further comprises matching a deformed portion of the line that is bowed inward as being the portion of the line that is over the iris.

15. The system of claim 2, wherein the system is a wearable computer and the display is a head-mounted display.

16. The system of claim 12, wherein the system further provides a position and an orientation to the processor.

* * * * *